US008736002B2

(12) United States Patent
Graf et al.

(10) Patent No.: US 8,736,002 B2
(45) Date of Patent: May 27, 2014

(54) SENSOR MOUNTED IN FLIP-CHIP TECHNOLOGY AT A SUBSTRATE EDGE

(75) Inventors: Markus Graf, Zürich (CH); Werner Hunziker, Stäfa (CH); Franziska Brem, Küshacht (CH); Felix Mayer, Stäfa (CH)

(73) Assignee: Sensirion AG, Stafa (CH)

( * ) Notice: Subject to any disclaimer, the term of this patent is extended or adjusted under 35 U.S.C. 154(b) by 0 days.

(21) Appl. No.: 13/498,490

(22) PCT Filed: Nov. 18, 2009

(86) PCT No.: PCT/CH2009/000368
§ 371 (c)(1),
(2), (4) Date: May 11, 2012

(87) PCT Pub. No.: WO2011/060559
PCT Pub. Date: May 26, 2011

(65) Prior Publication Data
US 2012/0217593 A1    Aug. 30, 2012

(51) Int. Cl.
*H01L 29/84* (2006.01)
*H01L 21/50* (2006.01)
*H01L 23/12* (2006.01)

(52) U.S. Cl.
USPC ........... 257/415; 257/414; 257/678; 257/778; 257/E23.001; 257/E23.01; 257/E29.324; 438/48; 438/49; 438/51; 438/106; 438/108

(58) Field of Classification Search
USPC .................. 257/414, 415, 678, 778, E23.001, 257/E23.003, E23.01, E29.324; 438/48, 49, 438/51, 106, 108
See application file for complete search history.

(56) References Cited

U.S. PATENT DOCUMENTS 5,396,795 A * 3/1995 Araki .......................... 73/204.26
6,140,144 A 10/2000 Najafi et al.
(Continued)

FOREIGN PATENT DOCUMENTS

DE    19810060    11/1998
DE    19852967    5/2000
(Continued)

OTHER PUBLICATIONS

"Thermal CMOS Anemometers, A Thesis submitted to the Swiss Federal Institute of Technology Zurich for the degree of Doctor of Natural Causes", presented by Felix Mayer 1998, Abstract p. 5, Zusammenfassung p. 7, 6.2 Flip-Chip as a Sensor Packaging Technology, p. 75.

(Continued)

*Primary Examiner* — Peniel M Gumedzoe
(74) *Attorney, Agent, or Firm* — Cooper & Dunham LLP

(57) ABSTRACT

The sensor assembly comprises a substrate (1), such as a flexible printed circuit board, and a sensor chip (2) flip-chip mounted to the substrate (1), with a first side (3) of the sensor chip (2) facing the substrate (1). A sensing area (4) and contact pads (5) are integrated on the first side (3) of the sensor chip (2). Underfill (18) and/or solder flux is arranged between the sensor chip (2) and the substrate (1). The sensor chip (2) extends over an edge (12) of the substrate (1), with the edge (12) of the substrate (1) extending between the contact pads (5) and the sensing area (4) over the whole sensor chip (2). A dam (16) can be provided along the edge (12) of the substrate (1) for even better separation of the underfill (18) and the sensing area (4). This de sign allows for a simple alignment of the sensor chip on the substrate (1) and prevents underfill (18) from covering the sensing area (4).

17 Claims, 3 Drawing Sheets

(56) References Cited

U.S. PATENT DOCUMENTS

| | | | |
|---|---|---|---|
| 6,690,569 | B1 | 2/2004 | Mayer et al. |
| 7,028,531 | B2 | 4/2006 | Nikolaus |
| 7,256,059 | B2 * | 8/2007 | Lu et al. .......................... 438/25 |
| 2004/0259329 | A1 | 12/2004 | Boyle et al. |
| 2005/0104186 | A1 | 5/2005 | Yang et al. |
| 2006/0177349 | A1 | 8/2006 | Thaysen et al. |
| 2007/0275495 | A1 | 11/2007 | Mayer et al. |
| 2008/0250847 | A1 | 10/2008 | Kitani et al. |
| 2012/0217593 | A1 | 8/2012 | Graf et al. |
| 2012/0267731 | A1 | 10/2012 | Graf et al. |

FOREIGN PATENT DOCUMENTS

| | | |
|---|---|---|
| DE | 102005037948 | 2/2007 |
| WO | WO 9827411 | 6/1998 |

OTHER PUBLICATIONS

M.E. Poplawski, R.W. Hower, and R.B. Brown, "A Simple Packaging Process for Chemical Sensors", Solid-State Sensor and Actuator Workshop, Hilton Head, South Carolina, Jun. 13-16, 1994.

C Li, F.E. Sauser, R.G. Azizkhan, C.H. Ahn and I. Papautsky, "Polymer flip-chip bonding of pressure sensors on a flexible Kapton film for neonatal catheters", J. Micromech. Microeng. 15 (2005) 1729-1735.

Communication from the Examining Division issued on Apr. 2, 2013 by the European Patent Office in connection with European Patent Application No. 09756135.1.

R. Fillion, "Advanced Packaging Technology for Leading Edge Microelectronics and Flexible Electronics", MSE 542, Cornell University.

International Search Report in PCT/CH2009/000368.

* cited by examiner

SENSOR MOUNTED IN FLIP-CHIP TECHNOLOGY AT A SUBSTRATE EDGE

TECHNICAL FIELD

The invention relates to a sensor assembly comprising a substrate and a sensor chip flip-chip mounted to the substrate as well as to a method for manufacturing such a sensor.

BACKGROUND ART

Flip-chip mounting of sensor chips to substrates allows for a simple and efficient manufacturing of sensor assemblies, such as e.g. described in WO 98/27411, where a sensor chip having a sensing area integrated on a first side thereof is mounted to a substrate. The sensing area is structured to measure at least one parameter of the environment, such as environmental humidity or pressure, and has therefore to be accessible. For this reason, a window of the substrate is arranged opposite to the sensing area. Contact pads integrated on the first side of the sensor chip can be used to establish electrical contacts between the sensor chip and the substrate during flip-chip mounting.

Typically, and also as shown in WO 98/27411, the gap between the sensor chip and the substrate is filled by a filler material, the so-called "underfill". The underfill is typically applied as a liquid to one or two edges of the sensor chip after flip-chip mounting, and the liquid is then drawn into the gap using capillary forces and it is subsequently hardened.

In order to prevent the underfill from covering the sensing area, the sensor assembly of WO 98/27411 is provided with a dam extending around the sensing area and the window. Similar dams can be useful for preventing solder flux from covering the sensing area. When flip-chip mounting the sensor chip to the substrate, care must be taken to properly align the window in the substrate, the dam and the sensing area.

DISCLOSURE OF THE INVENTION

The problem to be solved by the present invention is to provide an assembly of the type mentioned above that can be manufactured easily.

This problem is solved by the sensor assembly of claim 1. Accordingly, the sensing area of the sensor chip is arranged in a "sensor section" of the chip, while the contact pads are arranged in a "contact section" of the chip. The sensor chip extends over an edge of the substrate, wherein the edge of the substrate extends between said sensor section and said contact section, namely over the whole sensor chip from a first edge of the sensor chip to a second edge of the sensor chip.

This results in a robust design that allows for large positioning tolerances between the sensor chip and the edge of the substrate, in particular in a direction parallel to the edge.

The invention also relates to a method for manufacturing this type of sensor comprising the steps of flip-chip mounting the sensor chip to the substrate with said sensor chip extending over the edge of said substrate, wherein the edge of said substrate extends between the sensor section and the contact section of the sensor chip over the whole sensor chip, namely from the first edge of said sensor chip to the second edge of said sensor chip, and applying the underfill or solder flux between said contact section and said substrate.

The edge of the substrate forms a capillary barrier for the underfill or solder flux when the same is filled into the gap between sensor chip and substrate. This barrier is arranged between the underfill or solder flux and the sensing area, separating the same.

For an even more reliable retention of the underfill or solder flux, a dam is advantageously arranged at the edge of the substrate. The dam extends between the sensor chip and the substrate, i.e. it blocks the gap between the sensor chip and the substrate for the underfill or solder flux, thus that the underfill or solder flux is bordered and blocked by the dam. In other words, the dam prevents the underfill or solder flux from covering the sensing area of the sensor chip.

Advantageously, the dam extends from the first edge of the sensor chip to its second edge, thereby blocking any access of the underfill or solder flux to the sensing section of the sensor chip.

Also, the dam can advantageously extend over the edge of the substrate, such that no gap between sensor chip and substrate exists at the side of the dam that faces the sensing area. The absence of such a gap lessens the probability of underfill or solder flux seeping into the sensing section of the sensor chip.

The sensing area can e.g. comprise a humidity sensor and/or a pressure sensor. This type of sensor needs to be in direct contact with its environment.

The invention can advantageously be used for applications where costs are to be kept low, such as in consumer electronics devices and computer equipment, such as hard disk drives.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

The Sensor Chip:

The sensor assembly described below comprises a sensor chip with a sensing area integrated thereon. The sensor chip is advantageously a semiconductor chip, but it may e.g. also be a glass or ceramics chip. Semiconductor chips have the advantage that they allow for direct integration of further circuitry thereon.

The sensing area can e.g. comprise a humidity sensor and/or a pressure sensor. It is e.g. formed by a flexible membrane of a pressure sensor or a moisture adsorbing material and a set of electrodes in the case of a humidity sensor.

A pressure sensor can e.g. be structured as disclosed in EP 1 860 418, the disclosure of which is incorporated herein by reference. In particular, the present invention is especially suited for absolute pressure sensors.

A humidity sensor can e.g. be structured as disclosed in U.S. Pat. No. 6,690,569, the disclosure of which is incorporated herein by reference.

As e.g. described in U.S. Pat. No. 6,690,569, in addition to a sensing area and contact pads, the sensor chip may also have further elements integrated thereon, in particular passive and active circuitry, such as amplifiers, filters, A/D- or D/A-converters, digital processing circuitry, etc.

The Substrate:

The assembly described below further comprises a substrate. The substrate is typically a printed circuit board having conducting leads mounted thereon. Advantageously, the substrate is a flexible printed circuit board. The term "flexible printed circuit board" refers to an electrically insulating substrate that has circuit leads integrated thereon and that can be reversibly bent to a radius of 1 cm or smaller.

FIRST EMBODIMENT

Figure 1:
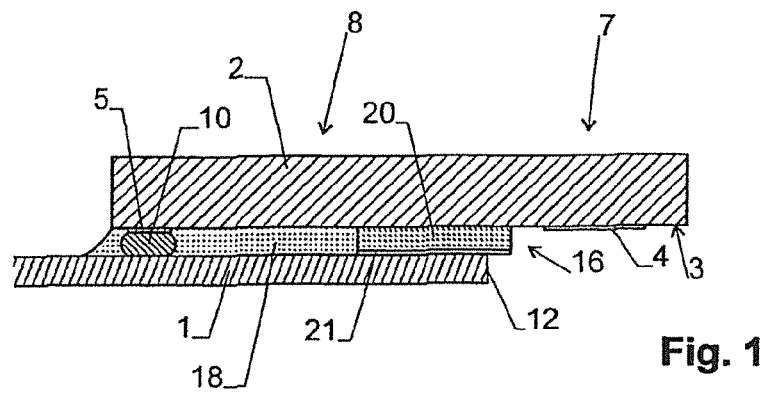
FIG. 1 shows a sectional view of a first sensor assembly.
Figure 2:
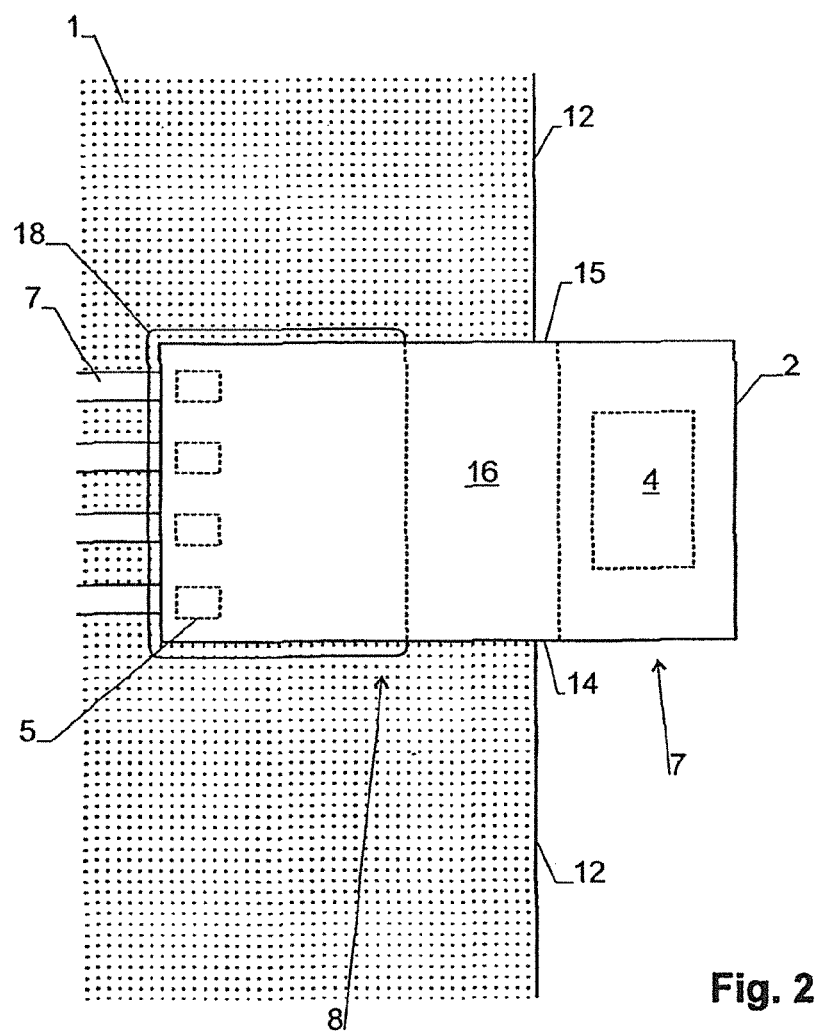
FIG. 2 shows a top view of the sensor assembly of FIG. 1.

FIGS. 1 and 2 show a sensor assembly according to a first embodiment of the invention. It comprises a substrate 1 and a sensor chip 2 as described above. Sensor chip 2 is flip-chip mounted to substrate 1, with a first side 3 of sensor chip 2 facing substrate 1.

The sensing area 4 and the contact pads 5 are both integrated on first side 3 of sensor chip 2, together with any further components integrated on sensor chip 2. Sensing area 4 is arranged in a first section of substrate 1, in the following called the "sensing section 7", while the contact pads 5 are arranged in a second section of substrate 1, in the following called the "contact section 8".

The contact pads 5 are electrically connected to conducting leads 7 on substrate 1 by means of solder bumps 10 as it is known to the skilled person.

As can best be seen in FIG. 2, sensor chip 2 extends over an edge 12 of substrate 1. Edge 12 extends between sensing section 7 and contact section 8, and it extends over the whole width of sensor chip 2, i.e. from a first edge 14 to a second, opposite edge 15 thereof.

The sensor assembly further comprises a dam 16 located at edge 12. In the embodiment of FIGS. 1 and 2, dam 16 extends over edge 12 of substrate 1, i.e. edge 12 of substrate 1 divides dam 16 into two parts, with a first part lying against substrate 1 and a second part extending freely over edge 12.

In a direction parallel to edge 12 of substrate 1, dam 16 extends from the first edge 14 of sensor chip 2 to the second edge 15 of sensor chip 2. In a direction perpendicular to substrate 1, dam 16 extends substantially all the way between sensor chip 2 and substrate 1. Hence, dam 16 forms a full barrier for the underfill.

The underfill 18 is arranged between sensor chip 2 and substrate 1, namely in contact section 8 of sensor chip 2, and is laterally bordered by dam 16.

Figure 3:
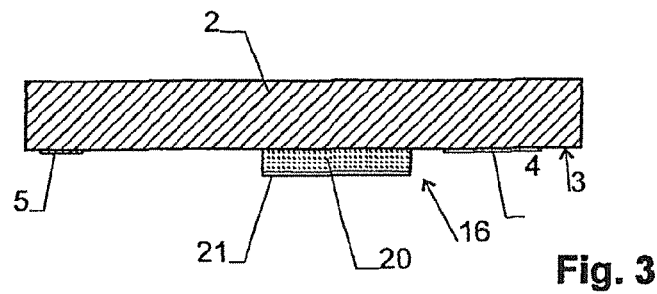
FIG. 3 shows a first manufacturing step of a sensor assembly.
Figure 4:
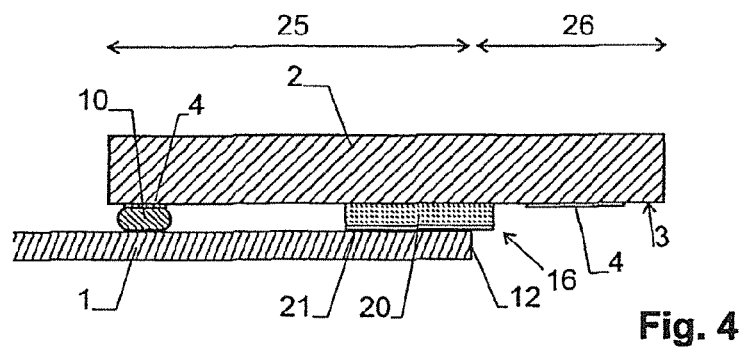
FIG. 4 shows a second manufacturing step of a sensor assembly

FIGS. 3 and 4 show the steps for manufacturing the sensor assembly.

First, sensor chip 2 is provided, with sensing area 4 and contact pads 5 integrated on its first side 3. Next, dam 16 is applied to first side 3. Dam 16 has a height substantially equal to the solder bumps 10 that are formed during the later flip-chip mounting step. It is advantageously formed at least partially of a photoresist, in particular SU-8, thus that it can be structured easily.

The term "photoresist" is to be understood as any material that is structured by irradiation and subsequent selective removal of irradiated or non-irradiated parts.

In the embodiment shown in FIGS. 1, 3 and 4, dam 16 comprises a first layer 20, which is advantageously formed by the photoresist mentioned above, and a second layer 21, which is advantageously an adhesive for being bonded to substrate 1. First layer 20 extends from sensor chip 2 to second layer 21, and second layer 21 extends, in the final assembly, from first layer 20 to substrate 1.

In a next step, the parts shown in FIG. 3 are flip-chip mounted to substrate 1 and the solder bumps 10 are formed to create the electrical connections between the contact pads 5 and the leads 7. At the same time, dam 16 is bonded to substrate 1, in the embodiment shown here by means of second layer 21. As mentioned, second layer 21 is advantageously an adhesive. For example, it can be applied to either first layer 21 or substrate 1 prior to flip-chip mounting. It may be a glue that bonds upon contact, or it may be a hot-melt adhesive that creates a bond at the elevated temperatures (typically around 260° C.) during flip-chip mounting. Also, layer 21 can be a UV-curable adhesive, which can be cured by UV-irradiation through substrate 1, or a snap-curable adhesive, which can be cured by heating above a threshold temperature.

As mentioned above, the height of dam 16 is advantageously substantially equal to the height of the solder bumps 10 formed during flip-chip mounting such that sensor chip 2 is aligned substantially parallel to substrate 1. Optionally, dam 16 may be of a material that is softened or even liquefied at the temperatures used during flip-chip mounting, which allows to improve this alignment by adjusting the positioning angle of sensor chip 2.

As can best be seen from FIGS. 2 and 4, edge 12 of substrate 1 divides sensor chip 2 into two parts 25 and 26 of unequal area, with contact section 8 lying in the larger part 25 and sensing area 4 lying in the smaller part 26. This design prevents sensor chip 25 from toppling over edge 12 and obviates the need for supporting the free end of sensor chip 1 during flip-chip mounting.

After flip-chip mounting, underfill 18 is applied, in liquid form, along the edge of sensor chip 2 in the region of contact section 8, drawn into the gap between sensor chip 2 and substrate 1, and hardened. As described above, the blocking action of dam 16 as well as the capillary stop formed by edge 12 prevent underfill 18 from covering sensing area 4.

SECOND EMBODIMENT

Figure 5:
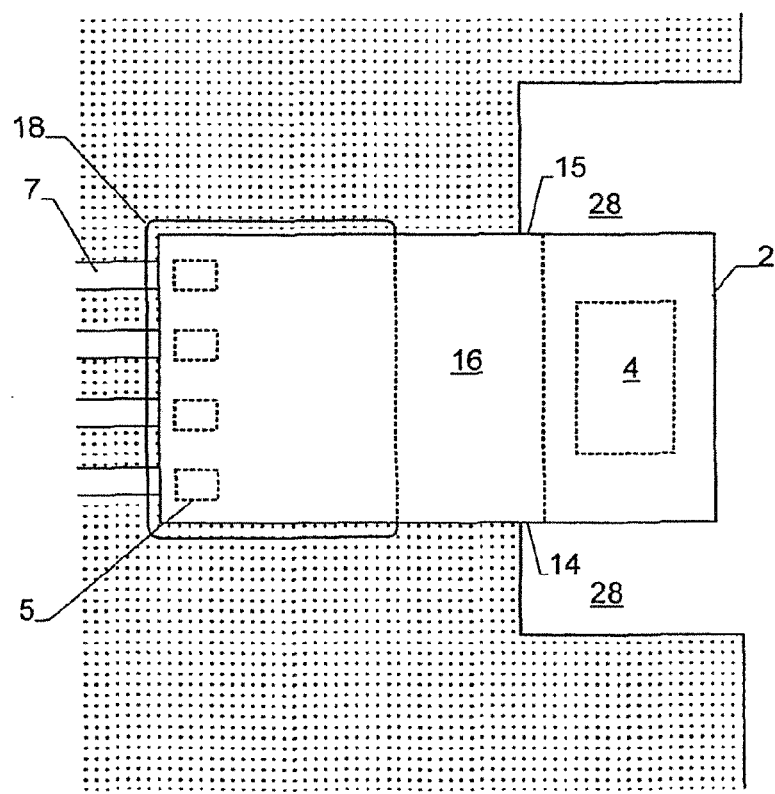
FIG. 5 shows a top view of a second sensor assembly.

FIG. 5 shows a second embodiment of a sensor assembly. The design of the embodiment of FIG. 5 is the same as the one of FIG. 2 and merely differs in the shape of edge 12. While edge 12 of FIG. 2 is part of a straight outer border of substrate 1, edge 12 of FIG. 5 is formed by the bottom of a recess 28 in the outer border of substrate 1. This design has the advantage that it provides better mechanical protection for the part of sensor chip 2 that extends beyond edge 12.

THIRD EMBODIMENT

Figure 6:
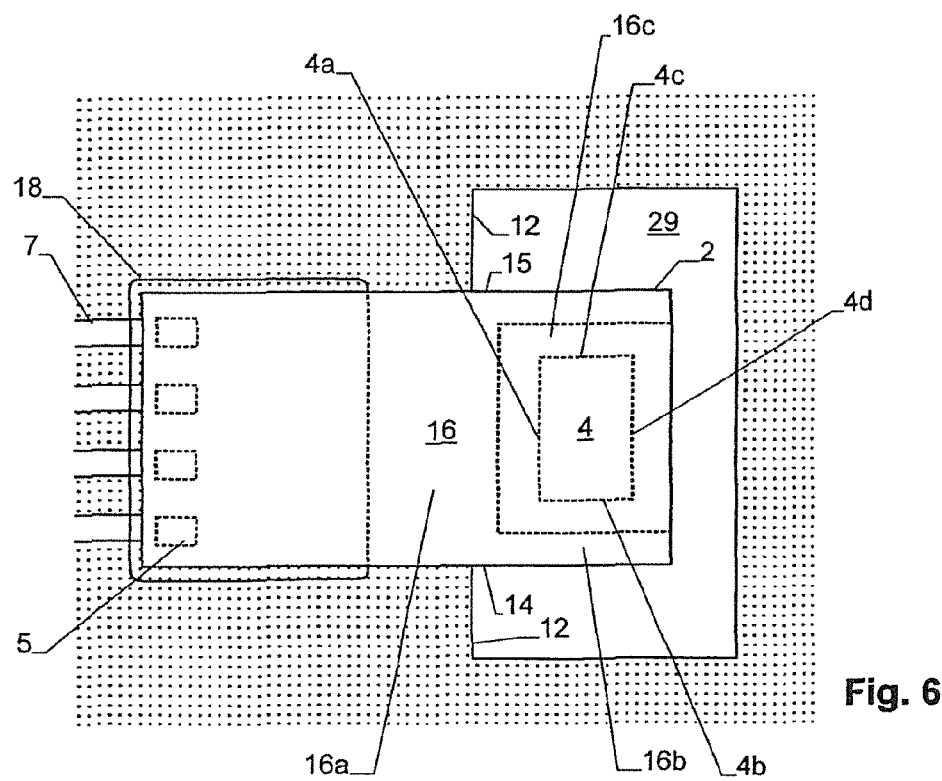
FIG. 6 shows a top view of a third sensor assembly.

The embodiment of FIG. 6 differs from the one of FIG. 2 in two aspects.

A first difference lies in the fact that edge 12 is not formed by a straight outer border of substrate 1, but rather by a window 29 that extends through substrate 1. Window 29 is again wider than sensor chip 2 thus that edge 12 extends all the way between first edge 14 and second edge 15 of sensor substrate 2.

A second difference lies in the design of dam 16. While, in the embodiment of FIG. 2, dam 16 extends as a straight bar from edge 14 to edge 15 of sensor chip 2, it has substantially U-shape in the embodiment of FIG. 6, with a base 16a, a first side section 16b and a second side section 16c. Base 16a extends along a first side 4a of sensing area 4, with side 4a extending parallel to edge 12. The two side sections 16b, 16c extend along second and third sides 4b, 4c of sensing area 4, with side sections 4b, 4c extending transversally to edge 12.

Arranging dam 16 along two transversal sides 4a, 4b of sensing area 4 has the advantage that it makes it even less likely that underfill (which is typically applied from two transversal sides of chip 2) enters sensing area 4. Arranging dam 16 also along third side 4c (parallel to second side 4b) of sensing area 4 provides even better protection.

It is even possible to arrange dam 16 also along fourth side 4d of sensing area 4, thereby fully enclosing the same.

FOURTH EMBODIMENT

Figure 7:
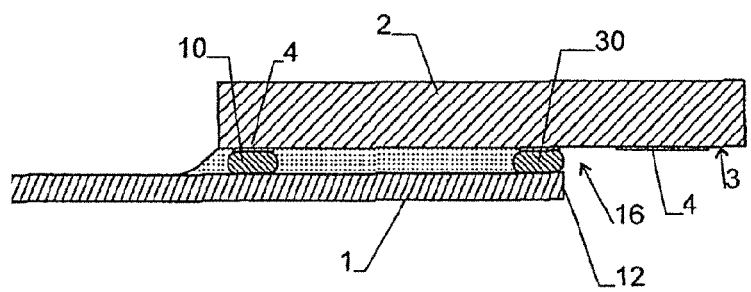
FIG. 7 shows a sectional view of a fourth sensor assembly.
Figure 8:
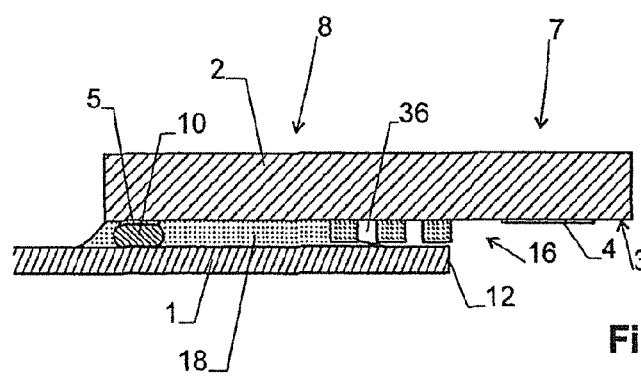
FIG. 8 shows a section view of a fifth sensor assembly.

The embodiment of FIG. 7 differs from the one of FIG. 1 in that dam 16 is formed by solder, advantageously by an elongate solder bump 30 extending substantially all the way between edges 14 and 15 of sensor chip 2. It may also be formed by a plurality of individual bumps arranged close to each other.

FIFTH EMBODIMENT

The embodiment differs from the one of FIG. 1 in that the underside of dam 16, i.e. the side facing substrate 1, comprises one or more recessed sections or gaps 36 that extend parallel to the dam 16. In that case, even if a small gap remains between the underside of dam 16 and substrate 1, underfill 18 may enter a first recess or gap 36, but will generally stop there. Hence, such recessed sections or gaps 36 allow to improve the sealing properties of dam 16 and can even obviate the need to fixedly connect dam 16 to substrate 1.

Notes

In the embodiments described above, underfill 18 has been arranged between sensor chip 2 and substrate 1, at least in the region of contact section 8. As mentioned, though, the dam can also be used to prevent solder flux, which is applied with the solder, from entering sensing area 4. Hence, the invention is also useful for sensor assemblies that do not use underfill.

The edge 12 of the above embodiments was straight. It must be noted, though, that edge 12 may also be curved, e.g. when being formed by a curved recess or rounded window of substrate 1.

While there are shown and described presently preferred embodiments of the invention, it is to be distinctly understood that the invention is not limited thereto but may be otherwise variously embodied and practiced within the scope of the following claims.

The invention claimed is:

1. A sensor assembly comprising:
a substrate,
a sensor chip flip-chip mounted to said substrate with a first side of said sensor chip facing said substrate,
a sensing area integrated on the first side of said sensor chip in a sensor section of said sensor chip, wherein said sensing area is structured to measure at least one parameter,
contact pads integrated on the first side of said sensor chip in a contact section of said sensor chip, wherein said contact pads are electrically connected to said substrate, wherein said sensor chip extends over an edge of said substrate, wherein the edge of said substrate extends between said sensor section and said contact section from a first edge of said sensor chip to a second edge of said sensor chip,
a dam arranged at the edge of said substrate between said contact section and said sensor section and extending between said sensor chip and said substrate, and
an underfill arranged between said contact section and said substrate, wherein said dam is arranged between said underfill and said sensing area.

2. The sensor assembly of claim 1 wherein said dam extends from the first edge of said sensor chip to the second edge of said sensor chip.

3. The sensor assembly of claim 1 wherein said dam extends over the edge of said substrate.

4. The sensor assembly of claim 1 wherein said dam comprises a photoresist, in particular SU-8.

5. The sensor assembly of claim 1 wherein said dam comprises a first layer and a second layer, wherein said first layer extends from said sensor chip and wherein said second layer extends to said substrate, wherein said second layer is an adhesive.

6. The sensor assembly of claim 1 wherein said dam comprises solder.

7. The sensor assembly of claim 1 wherein said dam extends along at least a first and a second side of said sensing area, with said first side of said sensing area extending parallel to the edge of said substrate and said second side of said sensing area extending transversally to said edge.

8. The sensor assembly of claim 7 wherein said dam encloses also at least a third side of said sensing area, with said third side being opposite to said second side.

9. The sensor assembly of claim 1, wherein said substrate is a flexible printed circuit board.

10. The sensory assembly of claim 1 wherein the edge of said substrate divides said sensor chip into two parts of unequal area, wherein said contact section lies in a larger one of said parts.

11. The sensor assembly of claim 1 wherein said sensing area comprises a humidity sensor and/or a pressure sensor.

12. The sensor assembly of claim 1 wherein said dam comprises one or more recesses or gaps extending parallel to said dam.

13. A method of manufacturing the sensor assembly of claim 1 comprising the steps of
flip-chip mounting said sensor chip to said substrate with said sensor chip extending over the edge of said substrate, wherein the edge of said substrate extends between said sensor section and said contact section over said whole sensor chip from the first edge of said sensor chip to the second edge of said sensor chip, and
applying underfill or solder flux between said contact section and said substrate.

14. The method of claim 13 comprising the steps of
applying the dam to the first side of said sensor chip prior to flip-chip mounting said sensor chip, and
applying said underfill or solder flux between said contact section, said substrate and said dam, with said dam being arranged between said underfill or solder flux and said sensing area.

15. The method of claim 14 wherein said dam is adhesively bonded to said substrate using a glue, hot-melt adhesive, a UV-curable adhesive or a snap-curable adhesive.

16. A sensor assembly comprising:
a substrate,
a sensor chip flip-chip mounted to said substrate with a first side of said sensor chip facing said substrate,
a sensing area integrated on the first side of said sensor chip in a sensor section of said sensor chip, wherein said sensing area is structured to measure at least one parameter, contact pads integrated on the first side of said sensor chip in a contact section of said sensor chip, wherein said contact pads are electrically connected to said substrate, wherein said sensor chip extends over an edge of said substrate, wherein the edge of said substrate extends between said sensor section and said contact section from a first edge of said sensor chip to a second edge of said sensor chip, and wherein the edge of said substrate is formed by a bottom of a recess in an outer border of said substrate.

17. A sensor assembly comprising:

a substrate, a sensor chip flip-chip mounted to said substrate with a first side of said sensor chip facing said substrate, a sensing area integrated on the first side of said sensor chip in a sensor section of said sensor chip, wherein said sensing area is structured to measure at least one parameter, contact pads integrated on the first side of said sensor chip in a contact section of said sensor chip, wherein said contact pads are electrically connected to said substrate, wherein said sensor chip extends over an edge of said substrate, wherein the edge of said substrate extends between said sensor section and said contact section from a first edge of said sensor chip to a second edge of said sensor chip, and wherein the edge of said substrate is formed by a window in said substrate.

\* \* \* \* \*